United States Patent
Tsoref et al.

(10) Patent No.: US 8,617,150 B2
(45) Date of Patent: *Dec. 31, 2013

(54) REFLECTANCE-FACILITATED ULTRASOUND TREATMENT

(76) Inventors: Liat Tsoref, Tel Aviv (IL); Yossi Gross, Moshav Mazor (IL)

( * ) Notice: Subject to any disclaimer, the term of this patent is extended or adjusted under 35 U.S.C. 154(b) by 810 days.

This patent is subject to a terminal disclaimer.

(21) Appl. No.: 12/780,240

(22) Filed: May 14, 2010

(65) Prior Publication Data

US 2011/0282249 A1 Nov. 17, 2011

(51) Int. Cl.
*A61B 18/14* (2006.01)

(52) U.S. Cl.
USPC .............................. 606/27; 606/41

(58) Field of Classification Search
USPC ............. 606/27–31, 41, 48–50; 600/439, 459
See application file for complete search history.

(56) References Cited

U.S. PATENT DOCUMENTS

| | | | |
|---|---|---|---|
| 4,619,247 A | 10/1986 | Inoue | |
| 5,735,280 A * | 4/1998 | Sherman et al. | 600/1 |
| 5,776,063 A | 7/1998 | Dittrich et al. | |
| 5,817,022 A | 10/1998 | Vesely | |
| 5,827,216 A | 10/1998 | Igo et al. | |
| 6,050,943 A | 4/2000 | Slayton et al. | |
| 6,064,902 A | 5/2000 | Haissaguerre et al. | |
| 6,241,727 B1 | 6/2001 | Tu et al. | |
| 6,425,877 B1 | 7/2002 | Edwards | |
| 6,605,084 B2 | 8/2003 | Acker et al. | |
| 6,635,054 B2 * | 10/2003 | Fjield et al. | 606/27 |
| 6,641,579 B1 | 11/2003 | Bernardi et al. | |
| 6,659,950 B2 | 12/2003 | Taheri | |
| 6,701,931 B2 | 3/2004 | Sliwa et al. | |
| 6,805,129 B1 | 10/2004 | Pless et al. | |
| 7,022,105 B1 | 4/2006 | Edwards | |
| 7,037,306 B2 | 5/2006 | Podany et al. | |
| 7,226,440 B2 | 6/2007 | Gelfand et al. | |
| 7,311,701 B2 | 12/2007 | Gifford et al. | |
| 7,326,201 B2 | 2/2008 | Fjield et al. | |
| 7,565,191 B2 | 7/2009 | Burbank et al. | |
| 7,662,099 B2 | 2/2010 | Podany et al. | |

(Continued)

FOREIGN PATENT DOCUMENTS

| | | |
|---|---|---|
| WO | 99/40957 A1 | 8/1999 |
| WO | WO 03/097162 | 11/2003 |

(Continued)

OTHER PUBLICATIONS

Buch E et al., "Intra-pericardial balloon retraction of the left atrium: A novel method to prevent esophageal injury during catheter ablation," Heart Rhythm 2008;5:1473-1475.

(Continued)

*Primary Examiner* — Michael Peffley
(74) *Attorney, Agent, or Firm* — Sughrue Mion, PLLC (57) ABSTRACT

Apparatus is provided that includes an ultrasound ablation system, which includes a reflection-facilitation element, configured to be placed at an extramyocardial site of a subject, and to provide an extramyocardial reflective region. The system further includes an ultrasound tool, which comprises at least one ultrasound transducer configured to be positioned within a heart chamber of the subject, and to ablate myocardial tissue by applying ultrasound energy to the myocardial tissue such that at least a portion of the transmitted energy is reflected by the reflective region onto the myocardial tissue. Other embodiments are also described.

11 Claims, 9 Drawing Sheets

(56) References Cited

U.S. PATENT DOCUMENTS

| | | |
|---|---|---|
| 8,197,409 B2 | 6/2012 | Foley et al. |
| 2001/0003798 A1 | 6/2001 | McGovern et al. |
| 2002/0091427 A1 | 7/2002 | Rappaport et al. |
| 2003/0018256 A1 | 1/2003 | Sasaki et al. |
| 2004/0034339 A1 | 2/2004 | Stoller |
| 2004/0097788 A1 | 5/2004 | Mourlas |
| 2004/0162507 A1 | 8/2004 | Govari et al. |
| 2004/0162550 A1 | 8/2004 | Govari et al. |
| 2005/0080469 A1 | 4/2005 | Larson et al. |
| 2005/0165298 A1 | 7/2005 | Larson et al. |
| 2005/0203410 A1 | 9/2005 | Jenkins |
| 2005/0251125 A1 | 11/2005 | Pless et al. |
| 2006/0009753 A1 | 1/2006 | Fjield et al. |
| 2006/0058711 A1 | 3/2006 | Harhen et al. |
| 2006/0100514 A1 | 5/2006 | Lopath |
| 2006/0184048 A1 | 8/2006 | Saadat |
| 2006/0241523 A1 | 10/2006 | Sinelnikov et al. |
| 2007/0004984 A1 | 1/2007 | Crum et al. |
| 2007/0093420 A1 | 4/2007 | Yeomans et al. |
| 2007/0239077 A1 | 10/2007 | Azhari et al. |
| 2007/0265610 A1 | 11/2007 | Thapliyal et al. |
| 2008/0015445 A1 | 1/2008 | Saadat |
| 2008/0033415 A1 | 2/2008 | Rieker et al. |
| 2008/0058682 A1 | 3/2008 | Azhari et al. |
| 2008/0091109 A1 | 4/2008 | Abraham |
| 2009/0048514 A1 | 2/2009 | Azhari et al. |
| 2009/0062790 A1 | 3/2009 | Malchano |
| 2009/0137900 A1* | 5/2009 | Bonner et al. ............... 600/424 |
| 2009/0192506 A9 | 7/2009 | Vaska et al. |
| 2009/0247912 A1 | 10/2009 | Warnking |
| 2009/0326511 A1 | 12/2009 | Shivkumar |
| 2010/0036292 A1 | 2/2010 | Darlington et al. |
| 2010/0130836 A1 | 5/2010 | Malchano |
| 2010/0168624 A1 | 7/2010 | Sliwa |
| 2011/0178541 A1 | 7/2011 | Azhari |
| 2011/0184322 A1 | 7/2011 | Brawer et al. |
| 2011/0251524 A1 | 10/2011 | Azhari et al. |
| 2011/0282203 A1 | 11/2011 | Tsoref et al. |
| 2012/0130363 A1 | 5/2012 | Kim et al. |
| 2012/0296240 A1 | 11/2012 | Azhari et al. |

FOREIGN PATENT DOCUMENTS

| | | |
|---|---|---|
| WO | 2006/072928 A2 | 7/2006 |
| WO | WO 2007/134258 | 11/2007 |
| WO | 2011/141918 A2 | 11/2011 |
| WO | 2012/120495 A2 | 9/2012 |

OTHER PUBLICATIONS

Cassak D, "Endosense: Facing technology and financing challenges in AF," In-Vivo: The Business & Medicine Report, 36-44, Mar. 2010.

Di Biase L et al., "Prevention of phrenic nerve injury during epicardial ablation: Comparison of methods for separating the phrenic nerve from the epicardial surface," Heart Rhythm 2009;6:957-961.

Matsuo S et al., "Novel technique to prevent left phrenic nerve injury during epicardial catheter ablation," Circulation 2008;117:e471.

Nakahara S et al., "Intrapericardial balloon placement for prevention of collateral injury during catheter ablation of the left atrium in a porcine model," Heart Rhythm 2010;7:81-87.

Shen J et al., "The surgical treatment of atrial fibrillation Heart Rhythm," vol. 6, No. 8S, Aug. Supplement 2009.

Sacher F et al., "Phrenic Nerve Injury After Catheter Ablation of Atrial Fibrillation," Indian Pacing Electrophysiol J. Jan.-Mar. 2007; 7(1): 1-6.

Schuessler RB et al., "Animal studies of epicardial atrial ablation," Heart Rhythm, vol. 6, No. 12S, S41-S45 December Supplement 2009.

Tanaka S et al., "Development of a new vascular endoscopic system for observing inner wall of aorta using intermittent saline jet" World Congress on Medical Physics and Biomedical Engineering, Sep. 7-12, 2009, Munich, Germany.

Tearney GJ et al., "Three-Dimensional coronary artery microscopy by intracoronary optical frequency domain imaging" JACC Cardiovasc Imaging. Nov. 2008; 1(6): 752-761.

William E. Cohn, et al., "Contrast pericardiography facilitates intrapericardial navigation under fluoroscopy", Ann Thorac Surg 2010; 90: 1537-40. Accepted for publication Jun. 7, 2010.

Srijoy Mahapatra, et al., "Pressure frequency characteristics of the pericardial space and thorax during subxiphoid access for epicardial ventricular tachycardia ablation", Heart Rhythm 2010; 7:604-609.

An Office Action dated Dec. 20, 2012, which issued during the prosecution of U.S. Appl. No. 11/653,115.

An Office Action dated Feb. 19, 2013, which issued during the prosecution of U.S. Appl. No. 13/010,555.

An International Search Report and a Written Opinion both dated Oct. 26, 2011, which issued during the prosecution of Applicant's PCT/IL11/003825.

An International Search Report and a Written Opinion both dated Sep. 17, 2012, which issued during the prosecution of Applicant's PCT/IL2012/000100.

An International Preliminary Report on Patentability dated Nov. 20, 2012, which issued during the prosecution of Applicant's PCT/IL11/003825.

International Search Report issued in PCT/IL13/50134 on Aug. 12, 2013.

* cited by examiner

REFLECTANCE-FACILITATED ULTRASOUND TREATMENT

FIELD OF THE APPLICATION

Embodiments of the present invention relate generally to treatment of tissue by application of energy thereto, and particularly to ablation of cardiac tissue by application of ultrasound energy.

BACKGROUND OF THE APPLICATION

Atrial fibrillation is a common cardiac arrhythmia involving the atria of the heart. During atrial fibrillation, the atria beat irregularly and out of coordination with the ventricles of the heart. Atrial fibrillation disrupts efficient beating of the heart and may result in blood clotting in the atrium leading to serious medical conditions such as strokes.

Atrial fibrillation is generally caused by abnormal electrical activity in the heart. During atrial fibrillation, electrical discharges may be generated by parts of the atria which do not normally generate electrical discharges, such as pulmonary vein ostia in the atrium. Pulmonary vein isolation is a common medical procedure for treatment of atrial fibrillation.

Ablation technologies currently include unipolar and bipolar techniques. The unipolar techniques employ various energy sources, including radiofrequency (RF), microwave, high intensity focused ultrasound (HIFU), laser, and cryogenic energy sources. The bipolar techniques employ RF energy.

U.S. Pat. No. 7,326,201 to Fjield et al. describes a collapsible ultrasonic reflector which incorporates a gas-filled reflector balloon, a liquid-filled structural balloon, and an ultrasonic transducer disposed within the structural balloon. Acoustic energy emitted by the transducer is reflected by a highly reflective interface between the balloons. In a cardiac ablation procedure, the ultrasonic energy is described as being focused into an annular focal region to ablate cardiac tissue extending in an annular path along the wall. Devices for stabilizing the balloon structure and for facilitating collapse and withdrawal of the balloon structure are also described.

U.S. Patent Application Publication 2006/0100514 to Lopath describes a cardiac ablation procedure, in which ultrasonic energy is emitted from an ultrasonic ablation device and is focused on myocardial tissue within the wall of the heart or within the wall of a blood vessel connected to the heart. Ultrasound attenuation of the cardiac tissue is described as being selectively increased by introducing microbubbles into the circulatory system of the subject so that the microbubbles enter the coronary arteries and pass into the myocardial tissue.

The following patents and patent applications may be of interest:
U.S. Pat. No. 5,776,063 to Dittrich et al.
U.S. Pat. No. 6,605,084 to Acker et al.
U.S. Pat. No. 6,635,054 to Fjield et al.
U.S. Pat. No. 7,311,701 to Gifford et al.
U.S. Pat. No. 7,565,191 to Burbank et al.
U.S. Patent Application Publication 2005/0080469 to Larson et al.
U.S. Patent Application Publication 2006/0241523 to Sinelnikov et al.
U.S. Patent Application Publication 2007/0239077 to Azhari et al.
U.S. Patent Application Publication 2008/0058682 to Azhari et al.
U.S. Patent Application Publication 2008/0033415 to Rieker et al.
U.S. Patent Application Publication 2009/0247912 to Warnking
PCT Publication WO 2003/097162 to Vortman et al.

The following references may be of interest:
Buch E et al., "Intra-pericardial balloon retraction of the left atrium: A novel method to prevent esophageal injury during catheter ablation," Heart Rhythm 2008; 5:1473-1475
Cassak D, "Endosense: Facing technology and financing challenges in AF," IN-VIVO: The Business & Medicine Report, 36-44, March 2010
Di Biase L et al., "Prevention of phrenic nerve injury during epicardial ablation: Comparison of methods for separating the phrenic nerve from the epicardial surface," Heart Rhythm 2009; 6:957-961
Matsuo S et al., "Novel technique to prevent left phrenic nerve injury during epicardial catheter ablation," Circulation 2008; 117:e471
Nakahara S et al., "Intrapericardial balloon placement for prevention of collateral injury during catheter ablation of the left atrium in a porcine model," Heart Rhythm 2010; 7:81-87
Shen J et al., "The surgical treatment of atrial fibrillation Heart Rhythm," Vol 6, No 8S, August Supplement 2009.
Sacher F et al., "Phrenic Nerve Injury After Catheter Ablation of Atrial Fibrillation," Indian Pacing Electrophysiol J. 2007 January-March; 7(1): 1-6.
Schuessler R B et al., "Animal studies of epicardial atrial ablation," Heart Rhythm, Vol. 6, No 12S, S41-S45, December Supplement 2009

SUMMARY OF APPLICATIONS

In some embodiments of the present invention, methods and apparatus are provided for application of ultrasound energy to tissue within a body of a subject. For some applications, the ultrasound energy is applied to treat cardiac arrhythmias, such as atrial fibrillation, ventricular fibrillation, and/or ventricular tachycardia. During a minimally invasive procedure, an ultrasound tool is advanced into an organ of the body, such as a heart chamber. The ultrasound tool comprises at least one ultrasound transducer that is configured to transmit treatment energy, e.g., high intensity focused ultrasound (HIFU), towards myocardial tissue, and in particular towards sites within myocardial tissue which are involved in triggering, maintaining, or propagating cardiac arrhythmias, e.g., in the case of atrial fibrillation, pulmonary vein ostia. The treatment energy applied to the myocardial tissue causes ablation of the tissue. As a result of the ablation, scars typically form in the ablated areas. The scars generally block abnormal electrical pulses generated in the pulmonary vein ostia from propagating into the heart chambers, thereby electrically isolating the pulmonary veins from the atrium and preventing cardiac arrhythmias.

For some applications, prior to application of the treatment energy, a reflection-facilitation element is placed at an extramyocardial site, in a vicinity of the myocardial tissue designated for treatment. The reflection-facilitation element provides a reflective region in the extramyocardial site. Typically, the extramyocardial site is within a "pericardial region," which, as used in the present application, including the claims, consists of one or more regions selected from the group consisting of: a region between the pericardium and the myocardium, a region between the visceral pericardium (also known as the epicardium) and the parietal pericardium, and a region outside the pericardium and in contact therewith. The treatment energy applied by the ultrasound transducer to the sites in the myocardial tissue is reflected from the extramyocardial reflective region back through the myocardial tissue. The treatment energy is thus directed at the myocardial site from two opposing directions, nearly doubling the applied energy, thereby resulting in enhanced ablation of the myocardial tissue. This technique enables the rapid formation of an effective transmural lesion having an increased depth within the myocardium (as viewed from within the heart) and/or increased homogeneity along the depth, compared to that which would be achieved in the absence of the reflection of the ultrasound energy.

For some applications, the reflection-facilitation element comprises a gas-delivery element, which provides the reflective region by delivering a gas to the extramyocardial site. The gas-delivery element, e.g., a needle, is typically inserted through the pericardium and is configured to deliver gas to create a gas-filled pocket within the pericardial region, as defined hereinabove. The gas has a lower density than that of the surrounding tissue within the body, thereby creating a change in acoustic impedance. Due to the change in acoustic impedance, ultrasound waves which reach the gas are reflected. Thus, the gas in the gas-inflated extramyocardial site serves as a reflector for the ultrasound energy. Typically, following inflation of the pericardium with gas, ultrasound energy is applied by the ultrasound transducer in the heart to the designated treatment site in the myocardial tissue that is adjacent to the gas-filled pericardium. The emitted energy reaches the designated treatment site and is reflected by the gas, such that the reflected ultrasound energy passes again through the treatment site.

There is therefore provided, in accordance with an application of the present invention, apparatus including an ultrasound ablation system, which includes:

a reflection-facilitation element, configured to be placed at an extramyocardial site of a subject, and to provide an extramyocardial reflective region; and an ultrasound tool, which includes at least one ultrasound transducer configured to be positioned within a heart chamber of the subject, and to ablate myocardial tissue by applying ultrasound energy to the myocardial tissue such that at least a portion of the transmitted energy is reflected by the reflective region onto the myocardial tissue.

For some applications, the chamber is a left atrium, and the ultrasound transducer is configured to be positioned within the left atrium.

For some applications, the ultrasound transducer is configured to apply the ultrasound energy as high intensity focused ultrasound (HIFU) energy.

For some applications, the ultrasound tool further includes an anchoring element, which is configured to temporarily stabilize the tool in the chamber. For example, the anchoring element may include at least one inflatable element, configured to be inflated such that the inflatable element temporarily stabilizes the tool by contacting an inner wall of a blood vessel.

For some applications, the reflection-facilitation element includes a gas-delivery element, configured to provide the reflective region by delivering a gas to the extramyocardial site.

For some applications, the extramyocardial site of the subject is within a pericardial region of the subject that consists of one or more regions selected from the group consisting of: a region between the pericardium and the myocardium, a region between the visceral pericardium and the parietal pericardium, and a region outside the pericardium and in contact therewith, and the reflection-facilitation element is configured to provide the reflective region within the pericardial region.

For some applications, the reflection-facilitation element includes an inflatable element. Alternatively or additionally, for some applications, the reflection-facilitation element includes an acoustic reflector, configured to be delivered to the extramyocardial site of the subject.

For some applications, the reflection-facilitation element is configured to be transthoracically delivered to the extramyocardial site of the subject.

For some applications, the ultrasound tool further includes an arm having a distal end, and the at least one ultrasound transducer is coupled to the distal end of the arm.

For some applications, the reflection-facilitation element includes a mechanical surgical retractor.

For some applications, the ultrasound transducer includes an array of ultrasonic elements.

For some applications, the system further includes a control unit, which is configured to monitor an ultrasonic parameter of the myocardial tissue. For some applications, the control unit is configured to perform an analysis of the parameter, and, responsively to the analysis, to drive the ultrasound transducer to cease ablating the myocardial tissue.

For some applications, the ultrasonic parameter is a time of flight of the ultrasound energy applied by the ultrasound transducer and reflected by the reflective region. For some applications, the control unit is configured to ascertain a temperature of the tissue responsively to the time of flight. For some applications, the control unit is configured to use signal processing to eliminate sinusoidal behavior exhibited by the time of flight due to atrial contractions. For some applications, the control unit is configured to use an average moving window to eliminate the sinusoidal behavior.

For some applications, the ultrasonic parameter is selected from the group consisting of: an amplitude of the ultrasound energy applied by the ultrasound transducer and reflected by the reflective region, a scatter intensity of the reflected ultrasound energy, sub-harmonics of the reflected ultrasound energy, second and higher harmonic reflections of the reflected ultrasound energy, an attenuation of the reflected ultrasound energy, and a non-linear parameter of the reflected ultrasound energy.

There is further provided, in accordance with an application of the present invention, apparatus including an ultrasound ablation system, which includes:

a reflection-facilitation element, configured to be placed within a heart chamber of a subject, and to provide an intracardiac reflective region; and an ultrasound tool, which includes at least one ultrasound transducer configured to be positioned at an extramyocardial site of the subject, and to ablate myocardial tissue by applying ultrasound energy to the myocardial tissue such that at least a portion of the transmitted energy is reflected by the reflective region onto the myocardial tissue.

For some applications, the chamber is a left atrium, and the reflection-facilitation element is configured to be placed within the left atrium, and to provide the intracardiac reflective region within the left atrium.

For some applications, the ultrasound transducer is configured to apply the ultrasound energy as high intensity focused ultrasound (HIFU) energy.

For some applications, the extramyocardial site of the subject is within a pericardial region of the subject that consists of one or more regions selected from the group consisting of: a region between the pericardium and the myocardium, a region between the visceral pericardium and the parietal pericardium, and a region outside the pericardium and in contact therewith, and the ultrasound transducer is configured to be positioned within the pericardial region.

There is still further provided, in accordance with an application of the present invention, a method including:

advancing, into a heart chamber of a subject, an ultrasound tool that includes at least one ultrasound transducer;

providing a reflective region at an extramyocardial site of the subject; and activating the ultrasound transducer to ablate myocardial tissue by applying ultrasound energy to the myocardial tissue such that at least a portion of the transmitted energy is reflected by the reflective region onto the myocardial tissue of the subject.

For some applications, providing the reflective region includes using a reflective-facilitation element to provide the reflective region.

For some applications, the chamber is a left atrium, and advancing includes advancing the ultrasound tool into the left atrium.

For some applications, activating includes activating the ultrasound transducer to apply the ultrasound energy as high intensity focused ultrasound (HIFU) energy.

For some applications, advancing the ultrasound tool includes temporarily stabilizing the ultrasound tool in the chamber using an anchoring element.

For some applications, providing the reflective region includes delivering a gas to the extramyocardial site.

For some applications, the extramyocardial site is within a pericardial region of the subject that consists of one or more regions selected from the group consisting of: a region between the pericardium and the myocardium, a region between the visceral pericardium and the parietal pericardium, and a region outside the pericardium and in contact therewith, and providing the reflective region includes providing the reflective region within the pericardial region.

For some applications, providing the reflective region includes inflating an inflatable element at the extramyocardial site with a fluid selected from the group consisting of: a gas, and a mixture of a liquid and a gas.

For some applications, providing the reflective region includes delivering an acoustic reflector to the extramyocardial site.

For some applications, providing the reflective region includes inserting a mechanical surgical retractor into the extramyocardial site.

For some applications, the ultrasound transducer includes an array of ultrasonic elements, and activating the ultrasound transducer includes activating the array of ultrasonic elements.

For some applications, activating further includes monitoring an ultrasonic parameter of the myocardial tissue. For some applications, activating further includes performing an analysis of the parameter, and, responsively to the analysis, ceasing ablating the myocardial tissue.

For some applications, the parameter is a time of flight of the ultrasound energy applied by the ultrasound transducer and reflected by the reflective region. For some applications, monitoring includes ascertaining a temperature of the tissue responsively to the time of flight. For some applications, monitoring includes using signal processing to eliminate sinusoidal behavior exhibited by the time of flight due to atrial contractions. For some applications, using the signal processing includes using an average moving window to eliminate the sinusoidal behavior.

For some applications, the ultrasonic parameter is selected from the group consisting of: an amplitude of the ultrasound energy applied by the ultrasound transducer and reflected by the reflective region, a scatter intensity of the reflected ultrasound energy, sub-harmonics of the reflected ultrasound energy, second and higher harmonic reflections of the reflected ultrasound energy, an attenuation of the reflected ultrasound energy, and a non-linear parameter of the reflected ultrasound energy.

There is additionally provided, in accordance with an application of the present invention, a method including:

providing a reflective region within a heart chamber of a subject;

positioning at least one ultrasound transducer at an extramyocardial site of the subject; and activating the ultrasound transducer to ablate myocardial tissue by applying ultrasound energy to the myocardial tissue such that at least a portion of the transmitted energy is reflected by the reflective region onto the myocardial tissue of the subject.

For some applications, providing the reflective region includes using a reflective-facilitation element to provide the reflective region.

For some applications, providing the reflective region includes inserting an inflatable element into the chamber, and inflating the inflatable element with a fluid selected from the group consisting of: a gas, and a mixture of a liquid and a gas.

For some applications, the chamber is a left atrium, and providing includes providing the reflective region within the left atrium.

For some applications, activating includes activating the ultrasound transducer to apply the ultrasound energy as high intensity focused ultrasound (HIFU) energy.

For some applications, the extramyocardial site of the subject is within a pericardial region of the subject that consists of one or more regions selected from the group consisting of: a region between the pericardium and the myocardium, a region between the visceral pericardium and the parietal pericardium, and a region outside the pericardium and in contact therewith, and positioning includes positioning the at least one ultrasound transducer within the pericardial region.

There is yet additionally provide, in accordance with an application of the present invention, a method including:

providing a reflective region at a far side of tissue of a subject; and ablating the tissue by applying ultrasound energy to a near side of the tissue such that at least a portion of the applied energy is reflected onto the tissue by the reflective region.

For some applications, providing the reflective region includes placing a reflective-facilitation element at the far side of the tissue, and using the reflective-facilitation element to provide the reflective region.

For some applications, providing the reflective region includes providing a gas at the far side.

The present invention will be more fully understood from the following detailed description of embodiments thereof, taken together with the drawings, in which:

DETAILED DESCRIPTION OF APPLICATIONS

Figure 1A:
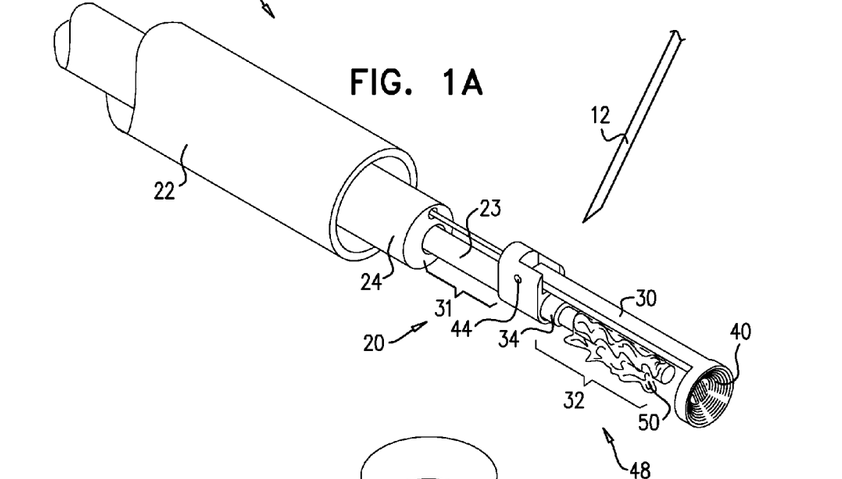
FIGS. 1A-B are schematic illustrations of an ultrasound ablation system, in accordance with some applications of the present invention.
Figure 1B:
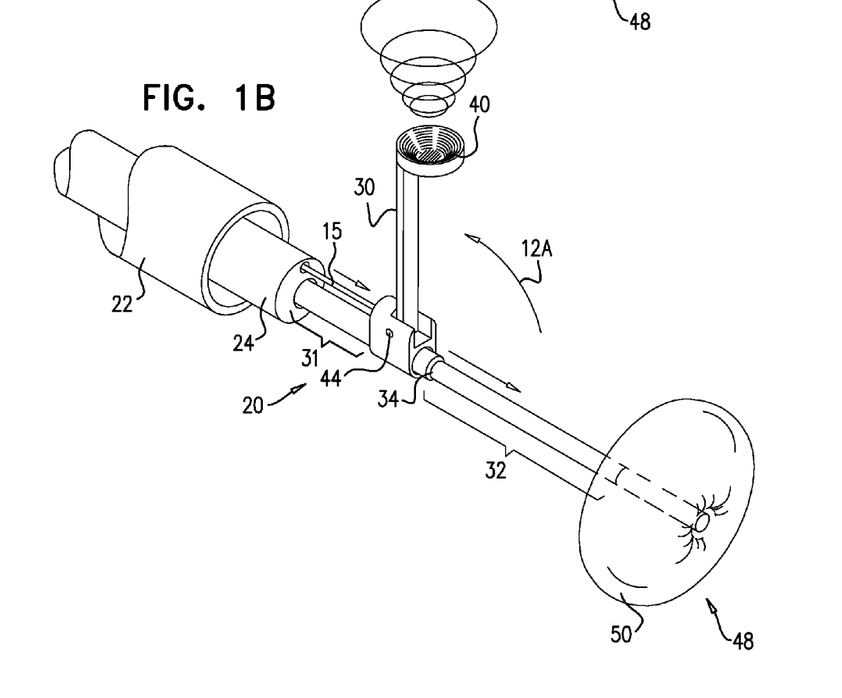

Reference is made to FIGS. 1A-B, which are schematic illustrations of an ultrasound ablation system 10, in accordance with some applications of the present invention. Ablation system 10 comprises an ultrasound tool 20 and a reflection-facilitation element 12, which, as described hereinbelow, provides a reflective region. Ultrasound tool 20 comprises at least one ultrasound transducer 40. Tool 20 typically further comprises a catheter 22, for facilitating advancement of the tool into a chamber of a heart of a subject. Tool 20 also may comprise a proximal shaft 24, which may house a distal shaft 23, which comprises a proximal portion 31, a distal portion 32, and a hinge 44. The hinge connects the proximal and distal portions, and facilitates rotation of different elements of tool 20. (In this context, in the specification and in the claims, "proximal" means closer to the orifice through which the tool is originally placed into the body, and "distal" means further from this orifice.)

For some applications, distal portion 32 comprises an arm 30 that is coupled to hinge 44. Arm 30 typically comprises, at a distal end thereof, the at least one ultrasound transducer 40. Tool 20 may comprise a plurality of arms 30 and any number of ultrasound transducers 40. For some applications, ultrasound transducer 40 is coupled to an element of tool 20 other than the arm.

For some applications, ultrasound tool 20 further comprises an anchoring element 48, which is configured to temporarily stabilize the tool during application of the treatment energy. For example, the anchoring element may temporarily anchor the distal end of tool 20 in a pulmonary vein. For some applications, as shown in the figures, anchoring element 48 comprises an inflatable element 50, e.g., comprising a balloon, which may be coupled to the distal end of distal portion 32 of shaft 23. Optionally the inflatable element is shaped so as to provide a passage therethrough for blood flow, such as described hereinbelow with reference to FIG. 5. Alternatively or additionally, for some applications, anchoring element 48 comprises a mechanical anchoring element. For example, the mechanical anchoring element may comprise a flexible metal element (e.g., comprising Nitinol) configured to engage the walls of the pulmonary vein, without blocking blood flow. For example, the metal element may have a U-shape or J-shape, such as provided on the Pulmonary Vein Ablation Catheter® (PVAC®) (Medtronic Ablation Frontiers LLC, Carlsbad, Calif.), or a flower-shaped element, such as provide by the Multi-Array Septal Catheter® (MASC®) (Medtronic Ablation Frontiers LLC, Carlsbad, Calif.).

Tool 20 is shown in FIG. 1A in a collapsed state thereof. In its collapsed state, tool 20 assumes a smaller dimension than in its expanded, operative state. Thus, in its collapsed state, the tool is configured for insertion into a blood vessel in a location remote from the heart and for advancement within a chamber of the heart. Accordingly, inflatable element 50 is shown in FIG. 1A in a deflated state.

Reference is now made to FIG. 1B, which shows tool 20 in the expanded, operative state thereof. Tool 20 is typically configured to be delivered to a location designated for treatment within a body of a subject, e.g., a chamber of the subject's heart. Once delivered to the location, tool 20 is transformed into the operative state as shown in FIG. 1B. In the operative state, hinge 44 typically facilitates deflection of arm 30, such that arm 30 is deflected laterally as indicated by arrow 12A (e.g., by 90 degrees, as shown) from a position that is aligned with a longitudinal axis of tool 20. Arm 30 may be deflected at any angle up to 180 degrees, such that ultrasound transducer 40 is aimed at any desired treatment site. For some applications, ultrasound transducer 40 is configured to emit high intensity focused ultrasound (HIFU) waves towards a target tissue. Optionally, a control wire 15 is controllable by a physician in order to adjust the angle of arm 30.

For some applications, distal portion 32 comprises a telescopically collapsible and extendable element 34, which facilitates the telescopic extension and collapse of distal portion 32.

Inflatable element 50 is shown in FIG. 1B in its inflated state.

Reference is made to FIGS. 2A-G, which are schematic illustrations of a system 10 for application of ultrasound energy to tissue within a body of a subject, in accordance with some applications of the present invention. Tool 20 is configured for treatment by ultrasound energy of a region within a body of a subject. Typically, tool 20 is configured for ablating tissue, e.g., cardiac tissue. For some applications, tool 20 is inserted into a chamber of the heart and disposed in an area that is adjacent to an orifice of a blood vessel 80, e.g., adjacent to a pulmonary vein ostium in the left atrium of the heart. Tool 20 is configured to ablate tissue in a vicinity of the orifice of the blood vessel in order to electrically isolate the blood vessel.

Figure 2A:
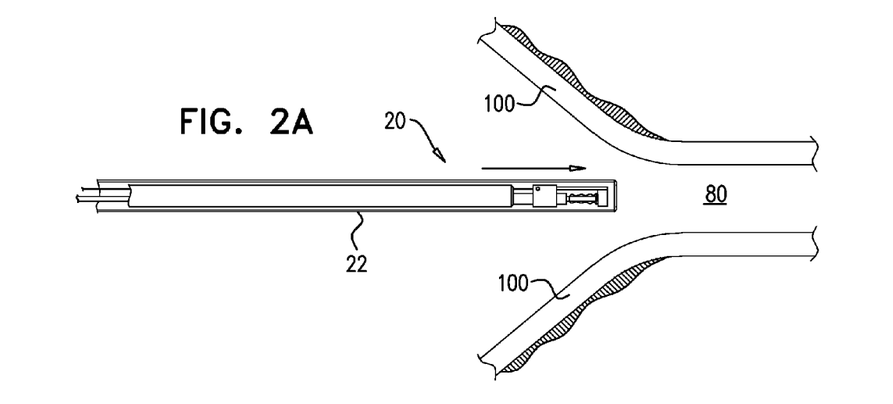
FIGS. 2A-F are schematic illustrations of the use of the ultrasound system of FIGS. 1A-B for application of ultrasound energy to tissue, in accordance with some applications of the present invention.

FIG. 2A shows tool 20 being advanced to a location within the heart that is adjacent to an orifice of a blood vessel. The tool is advanced in a collapsed state thereof, as described hereinabove with reference to FIG. 1A.

Figure 2B:
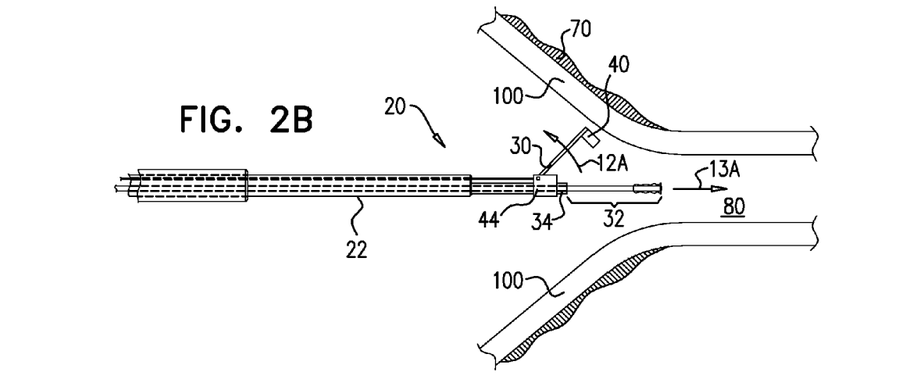
Figure 2C:
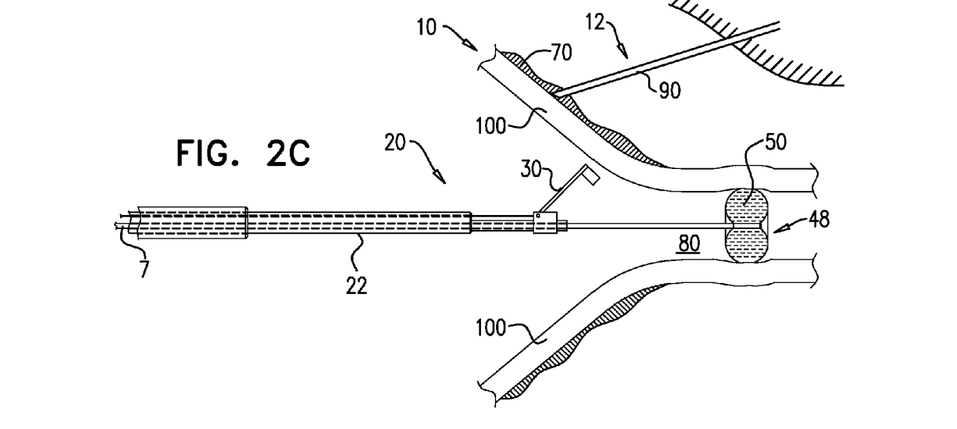

FIGS. 2B-C show the opening of tool 20 to an operative state. Tool 20 is shown disposed within a chamber of the heart, e.g., the left atrium. Tool 20 is located adjacent to an orifice of a blood vessel 80, e.g., a pulmonary vein ostium, and to cardiac tissue, e.g., an atrial wall 100. Hinge 44 typically facilitates deflection of arm 30 such that arm 30 is deflected laterally, as indicated by arrow 12A (e.g., by between 30 and 90 degrees, such as by 45 degrees, as shown) from a position that is aligned with a longitudinal axis of tool 20. The angle of deflection of arm 30 is typically controllable by the physician during a procedure. Deflection of arm 30 brings ultrasound transducer 40 into proximity of (e.g., in contact with or within a few millimeters of) the endocardium of cardiac tissue designated for ablation treatment, such that ultrasound transducer 40 is aimed at the designated site. There is generally no need for firm contact between ultrasound transducer and the endocardium. In some applications, the site designated for treatment is cardiac tissue in the atrial wall surrounding an orifice of a blood vessel, e.g., a pulmonary vein ostium.

For some applications, distal portion 32 of tool 20 is telescopically extended into blood vessel 80 in the direction indicated by an arrow 13A. For some applications, tool 20 comprises inflatable element 50, e.g., a balloon, coupled to the distal end of distal portion 32. For applications in which tool comprises anchoring element 48, during opening of tool 20 into an operative state, and subsequent application of treatment energy, the anchoring element stabilizes the tool against the wall of blood vessel 80 during application of treatment energy and rotation of arm 30 or another element of tool 20 (described hereinbelow). For example, for applications in which anchoring element 48 comprises inflatable element 50, inflatable element is inflated (by filling the inflatable element with fluid, i.e., a gas or a liquid) to apply pressure to a wall of blood vessel 80, in order to stabilize and maintain tool 20 in place. Inflatable element 50 may be inflated prior to deflection of arm 30, so as to stabilize and maintain tool 20 in place during the deflection of arm 30 and subsequent application of treatment energy. For some applications, inflatable element 50 comprises an annular inflatable element that surrounds a distal portion of tool 20.

It is to be noted that an inflation conduit 7 is coupled at a distal end thereof to inflatable element 50, and extends through a lumen of shaft 23 and toward distal portion 32 of tool 20. When the operating physician desires to inflate element 50, fluid (i.e., a gas or liquid) is delivered via the conduit toward inflatable element 50 from a fluid source that is disposed outside the body of the subject. The fluid may be pressurized.

Reference is still made to FIG. 2C. For some applications, prior to application of energy, reflection-facilitation element 12 is placed at an extramyocardial site, in a vicinity of the myocardial tissue designated for treatment. The reflection-facilitation element provides a reflective region in the extramyocardial site. For some applications, the reflection-facilitation element comprises a gas-delivery element 90 which delivers a gas to the extramyocardial site, e.g., within the pericardial region, as defined hereinabove. Gas-delivery element 90, which may, for example, comprise a needle, is typically inserted into or through the pericardium, and is configured to deliver gas to create a gas-filled pocket within the pericardial region, as defined hereinabove. For some applications, needle 90 is inserted through the central port, under the collarbone. Optionally, a small camera is inserted with the needle to provide image guidance during the insertion procedure.

Figure 2D:
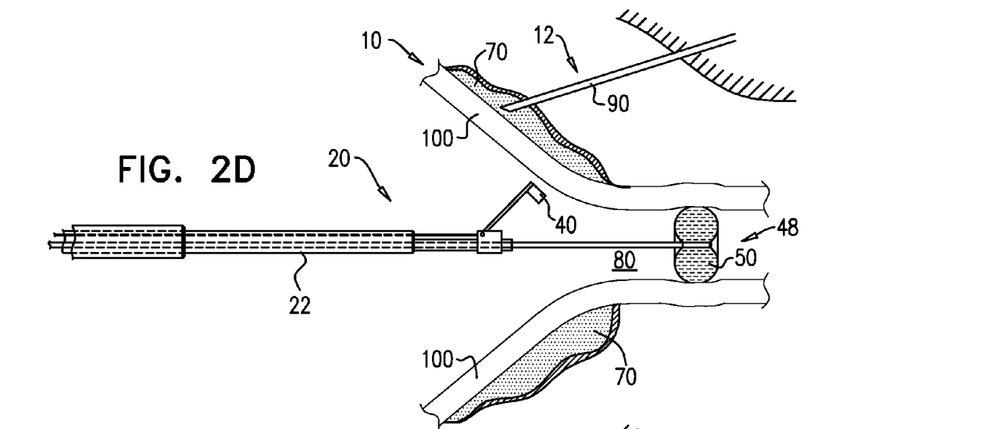

Reference is made to FIG. 2D, which shows system 10 positioned for applying ablating treatment to a target site in atrial wall 100. The pericardial region is shown in an inflated state, with gas having been delivered to the region between pericardium 70 and the myocardium. Alternatively, the pericardial region may be inflated by delivering the gas to the region between the visceral and parietal pericardial layers (configuration not shown). Arm 30 of tool 20 is deflected such that transducer 40 is aimed at a target site in atrial wall 100 designated for treatment. Additionally, for some applications, anchoring element 48 is deployed to stabilize and maintain tool 20 in place during subsequent application of treatment.

Figure 2E:
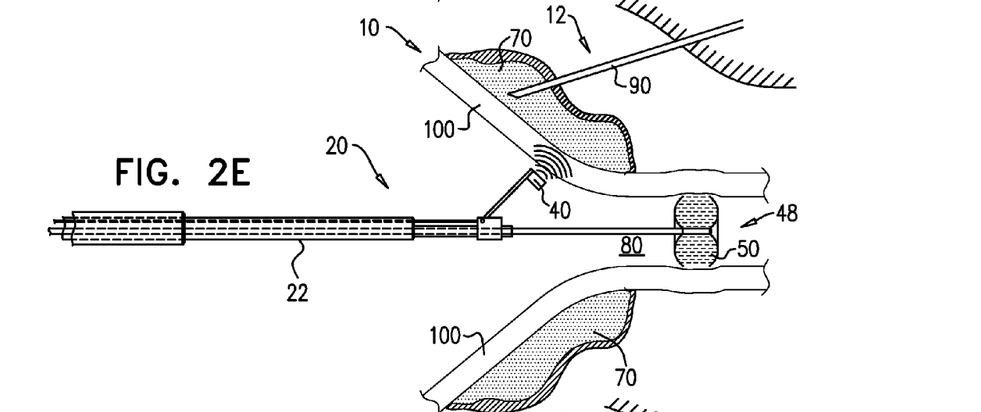

FIG. 2E is a schematic illustration of system 10 being operated to treat the subject. Ultrasound transducer 40 typically transmits high intensity focused ultrasound waves, directly heating the tissue in the acoustic focal volume (which may be cigar-shaped). For some applications, ultrasonic energy emitted by transducer 40 is focused by using a curved piezoelectric element and/or by using a lens and/or by using a plurality of ultrasound transducers 40. A focal point of transducer 40 is typically located in atrial wall 100, and the treatment energy transmitted by transducer 40 is generally capable of ablating myocardial tissue in atrial wall 100. For some applications, ultrasound transducer 40 is configured to transmit power at at least 10 watts, and/or less than 100 watts, e.g., between 10 and 100 watts, e.g., between 15 and 50 watts. Ablating ultrasound waves are shown passing through the tissue to reach a gas-filled region of pericardium 70. For some applications, ultrasound transducer 40 is configured to generate ultrasonic energy at a frequency having a value that is at least 100 kHz, e.g., at least 1.5 MHz, and/or no more than 10 MHz, e.g., no more than 5 MHz. At low frequencies (around 100-500 kHz), tissue destruction is primarily caused by cavitation, while at higher frequencies tissue destruction is primarily caused by a thermal effect. When creating the thermal effect, it is generally desirable to elevate the wall temperature to 60-80 degrees C.

Figure 2F:
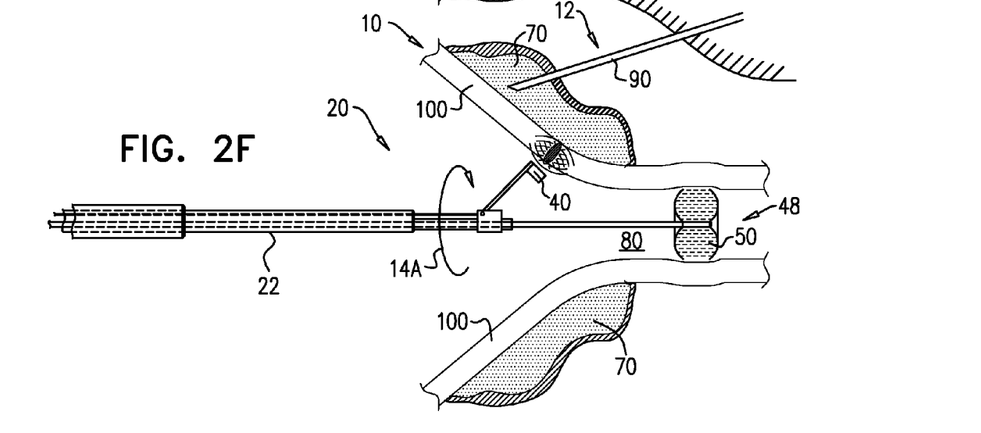

FIG. 2F shows ablating treatment energy being applied by ultrasound transducer 40 to a specific target site in atrial wall 100 and reaching a gas-filled region of pericardium 70. The gas is of lower density than the surrounding tissue in the body, thereby creating a change in acoustic impedance. Due to the change in acoustic impedance, the gas functions as a reflective region, similar to a mirror, along atrial wall 100 and ultrasound waves which reach the gas are reflected. Thus, ultrasound waves are typically reflected from the reflective region, back through myocardial tissue in atrial wall 100, resulting in temperature elevation and enhanced ablation of the myocardial tissue. Reflection of the ultrasound energy such that it passes through the tissue for a second time achieves what may be considered a bipolar effect, thereby increasing the thermal effect of the ultrasound energy, resulting in the rapid formation of an effective, transmural, long-lasting lesion in the tissue. Typically, the transmural lesion is formed rapidly at each radial site in 0.1-20 seconds, e.g., in about one second.

As shown in FIG. 2F, reflected return waves pass through the tissue generally simultaneously with the transmitted waves, increasing the amount of energy that passes through the tissue and achieving improved ablation of the tissue. Increased ablation of the tissue near the ostium of blood vessel 80 typically results in improved isolation of the blood vessel 80 and reduced occurrence of cardiac arrhythmia.

As shown in FIG. 2F, tool 20 (e.g., arm 30, another element of the tool, or the entire tool) can be rotated in a direction indicated by an arrow 14A (and/or in the opposite direction), such that ultrasound transducer 40 can be aimed at any desired location around an orifice of blood vessel 80. Rotation of tool allows circumferential ablation surrounding the orifice of blood vessel 80, e.g., the pulmonary vein ostium, such that blood vessel 80 is electrically isolated from other areas of the heart, blocking conduction of undesired pulses from blood vessel into the heart. Thus, tool 20 or an element thereof is typically rotated a full 360 degrees. Typically, anchoring element 48 does not rotate as arm 30 is rotated. For example, a hinge may be provided at distal portion 32 or at extendable element 34 that allows the rotation of arm 30 without the rotation of anchoring element 48.

Typically, following the creation of the first lesion in the ablation site in atrial wall 100, tool 20 is rotated slightly, e.g., by between 1 and 10 degrees (e.g., between 2.5 and 7.5 degrees), such that ultrasound transducer 40 is now aimed at an adjacent location of atrial wall 100, for creation of an additional lesion. This procedure is typically repeated until a 360-degree circumferential lesion surrounding the orifice of blood vessel 80 is formed. For some applications, transducer 40 is rotated slowly while continuously transmitting ultrasonic energy, thus creating a continuous circular lesion surrounding the orifice of blood vessel 80. For some applications, the rotation is performed manually by the physician performing the procedure. Alternatively, the rotation is performed by a motor. For some applications, system 10 comprises a control unit that senses when each individual lesion has been formed (e.g., by monitoring temperature, as described hereinbelow with reference to FIGS. 4A-B, e.g., by sensing that a desired temperature of 60 to 80 degrees has been obtained). Optionally, upon sensing that each lesion has been formed, the control unit drives the motor to rotate the tool or an element thereof, such that transducer 40 applies energy to a subsequent location.

Figure 2G:
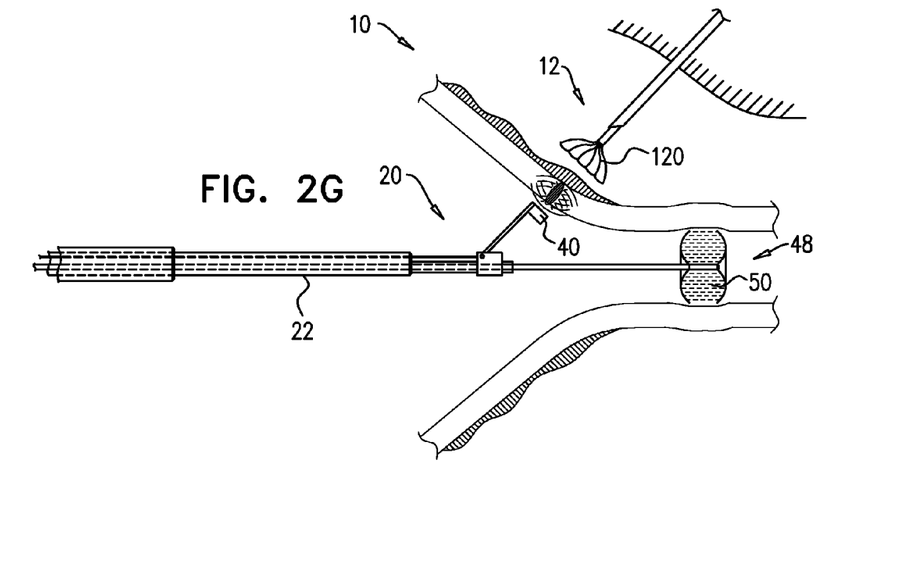
FIGS. 2G-J are schematic illustrations of alternative configurations of the system of FIGS. 1A-B, in accordance with respective applications of the present invention.

Reference is made to FIGS. 2G-J, which are schematic illustrations of alternative configurations of system 10, in accordance with respective applications of the present invention. For some applications, as shown in FIG. 2G, reflection-facilitation element 12 comprises a shaped acoustic reflector 120 (e.g., having a spherical, parabolic, or ellipsoidal shape), which may comprise, for example, a metal. Reflector 120 is typically placed at an extramyocardial site, e.g., within the pericardial region, as defined hereinabove, such as outside and typically in contact with the pericardium. The reflector causes ultrasound waves transmitted from transducer 40 to reflect back through the myocardial tissue, resulting in enhanced ablation of the myocardial tissue. Reflector 120 is placed facing ultrasonic transducer 40, and is moved as the transducer is rotated. Larger reflectors cover larger areas, and thus need be repositioned fewer times than smaller reflectors. For some applications, system 10 verifies proper positioning of reflector 120 by measuring the amplitude of the ultrasound echo received by transducer 40. The amplitude of the echo is small if the reflector is not properly positioned, and increases sharply when the reflector is properly positioned over the transducer.

Alternatively, reflection-facilitation element 12 comprises another material that has an acoustic impedance different from that of water, typically substantially different. For example, the element may comprise a sponge, an expanded polystyrene foam (e.g., Styrofoam®, Dow Chemical Company), or another material that contains a large amount of air. Ultrasound energy that is transmitted towards tissue of atrial wall 100 is reflected due to the different acoustic impedance, such that the return energy waves pass again through the tissue.

For some applications, reflection-facilitation element 12 comprises a mechanical surgical retractor, which is configured to separate the pericardium from the heart. The space thus created naturally fills with gas, thereby creating the reflective region. Surgical retractors are widely available from numerous manufacturers.

Figure 2H:
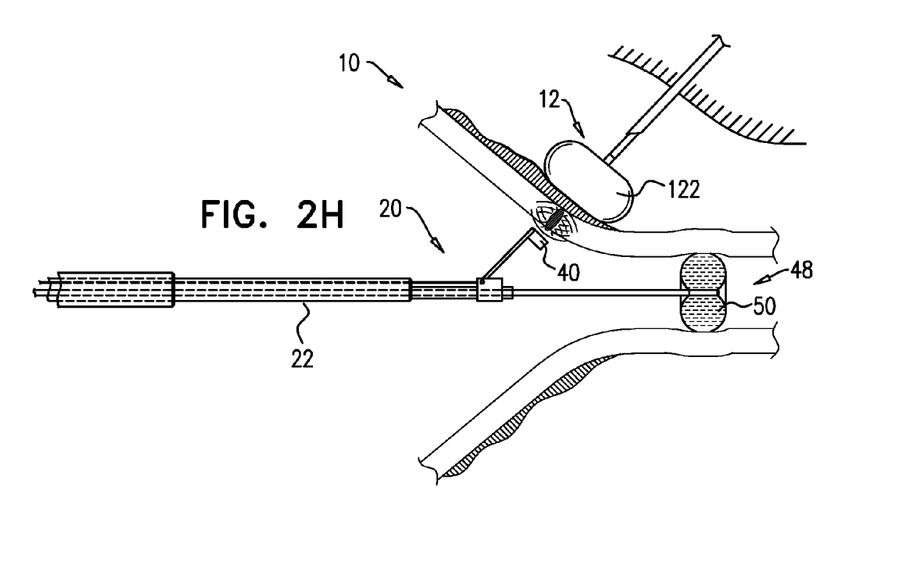

Reference is made to FIG. 2H. For some applications, reflection-facilitation element 12 comprises an inflatable element 122, e.g., a balloon. The inflatable element is inserted into the pericardial region, as defined hereinabove, typically between the pericardium 70 and atrial wall 100, or pressed against the outside of the pericardium. The inflatable element is typically inflated with a fluid having a lower density than water, such as a gas (e.g., carbon dioxide) or a mixture of fluid and gas. The low-density fluid functions as the reflective region described hereinabove. Ultrasound energy that is transmitted towards tissue of atrial wall 100 is reflected due to the fluid-filled (e.g., gas-filled) balloon, such that the return energy waves pass again through the tissue.

For some applications, inflatable element 122 is coupled to a double-channeled catheter. A first one of the channels is in fluid communication with the interior of the inflatable element, for delivering the fluid (gas or mixture of gas and liquid) to inflate the inflatable element. A second one of the channels is positioned in fluid communication with the pericardial region, typically the region between the pericardium and the myocardium. The second channel is used to deliver a gas to the pericardial region. For some applications, the channels are defined by two tubes, an inner tube positioned within an outer tube. For example, the inner tube may be in fluid communication with the inflatable element, and the outer tube may be in fluid communication with the pericardial region. For example, the outer tube may be shaped so as to define slots therethrough, through which the gas is injected into the pericardial region. For some applications, the inflatable element helps separate the membrane of the myocardium from that of the pericardium, functioning as a retractor.

Figure 2I:
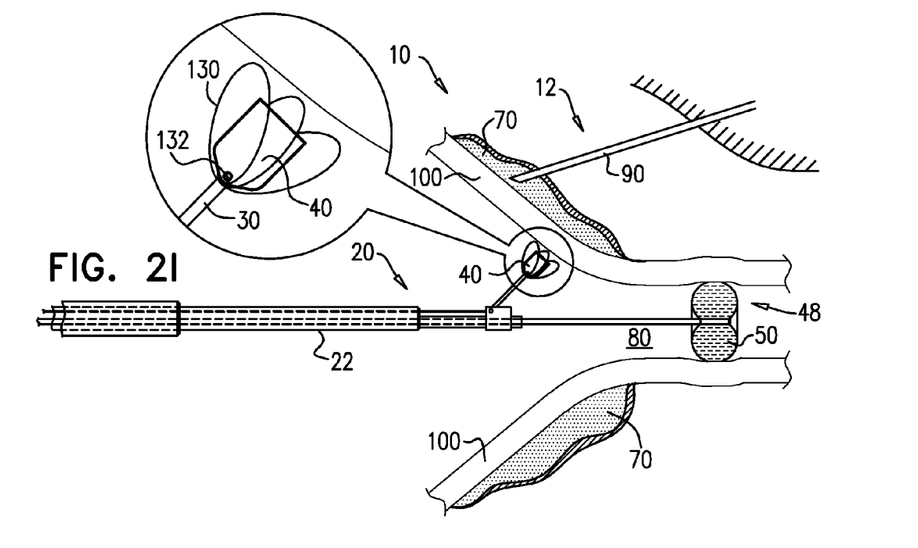

Reference is made to FIG. 2I. For some applications, arm 30 of tool 20 comprises one or more orientation elements 130, which are configured to orient ultrasound transducer 40 perpendicular to atrial wall 100, and, optionally, to position the transducer at a fixed distance from the atrial wall. The housing of ultrasound transducer 40 is configured to articulate with arm 30. For example, this articulation may be provided by a hinge 132 that couples the housing to the arm, or by one or more springs that couple the housing to the arm (configuration not shown). For some applications, the orientation elements may be arranged generally surrounding the ultrasound transducer, e.g., shaped like one or more petals of a flower. For some applications, the elements comprise a metal, e.g., Nitinol.

Figure 2J:
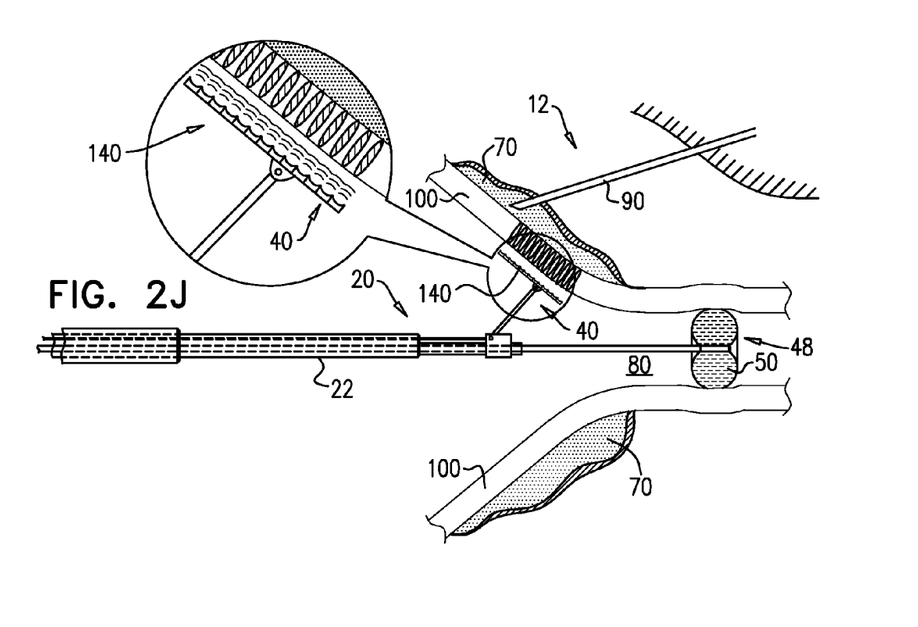

Reference is made to FIG. 2J. For some applications, ultrasound transducer 40 comprises an array 140 of ultrasonic elements, such as a linear array. Array 140 enables the ablation of a line, in addition to a circular lesion around the pulmonary veins. Alternatively, the line may be ablated by moving a single transducer linearly. Alternatively or additionally, a one- or two-dimensional array is used for beam forming and/or beam stirring.

Figure 3A:
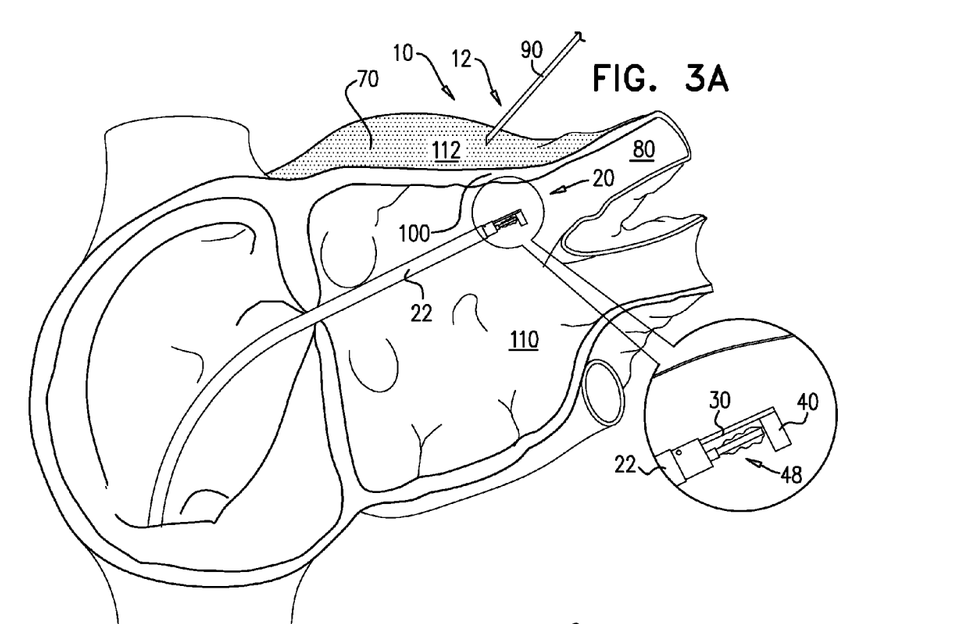
FIGS. 3A-C are schematic cross-sectional views of the atria showing operation of the system for application of ultrasound energy to tissue of the left atrium, in accordance with some applications of the present invention.
Figure 3B:
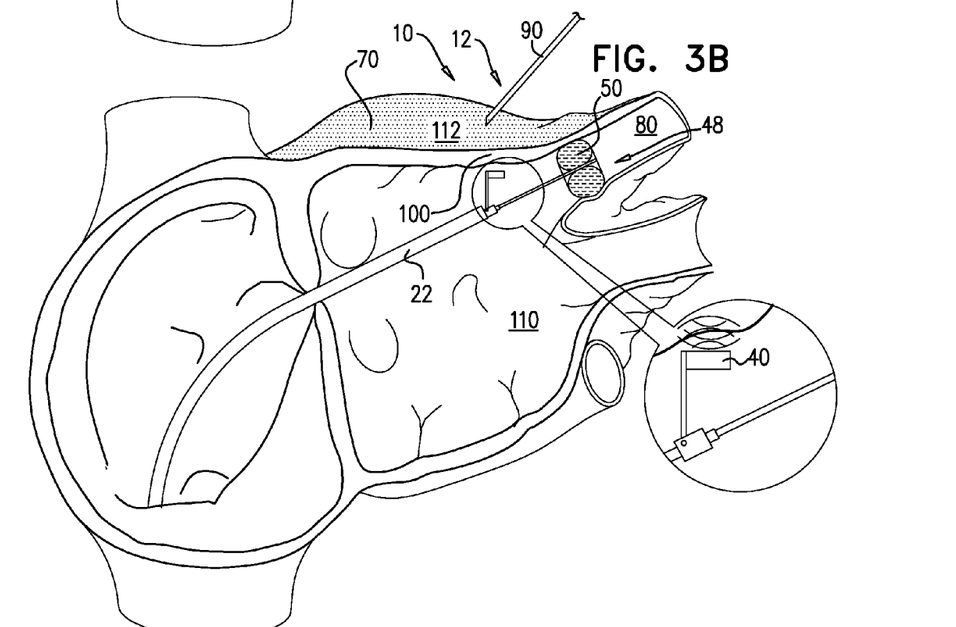
Figure 3C:
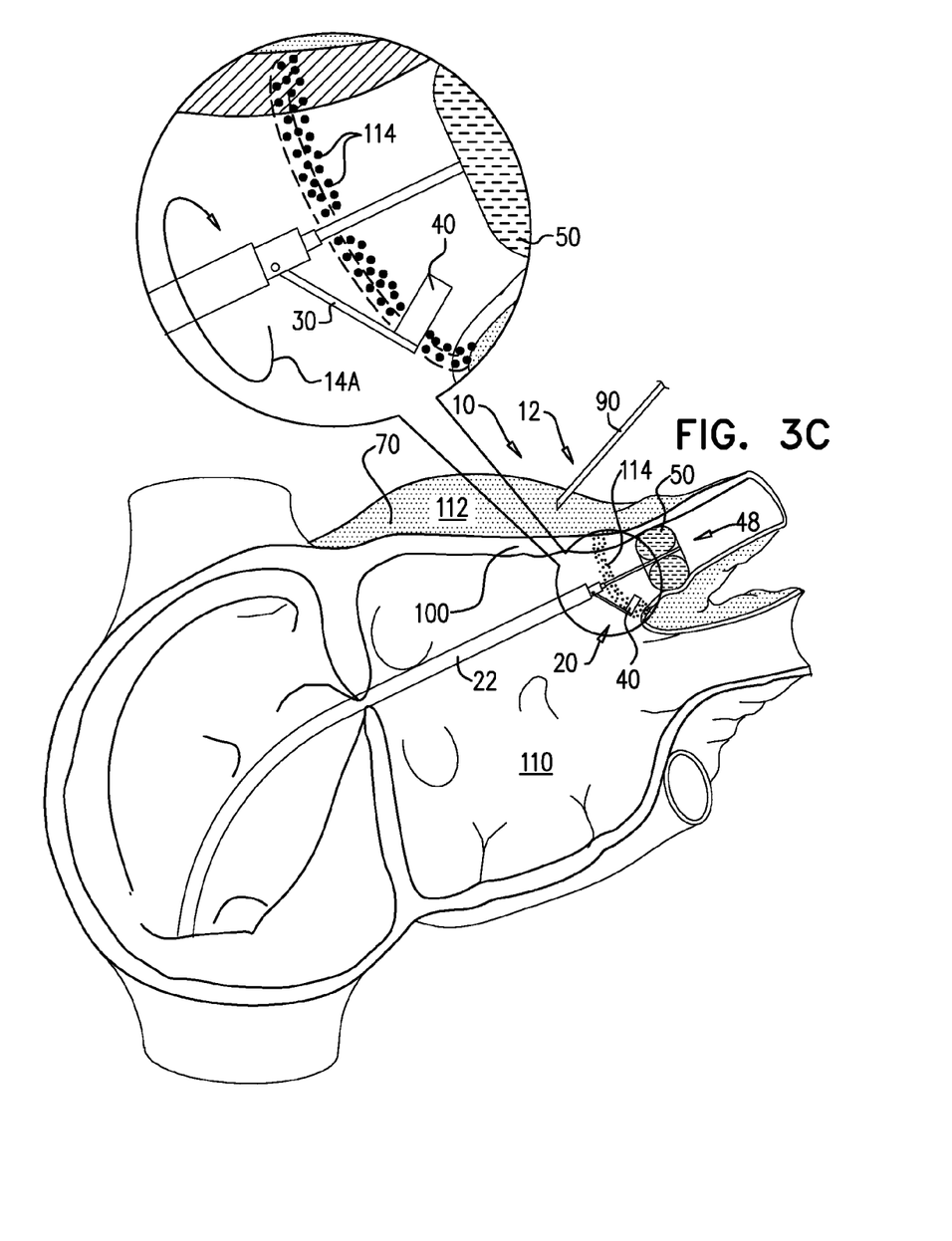

FIGS. 3A-C are schematic cross-sectional views of the atria showing operation of ultrasound ablation system 10 for application of energy, in accordance with some applications of the present invention. For some applications, system 10 is used for the treatment of atrial fibrillation. For such applications, system 10 is used to generate enhanced ablation in areas of pulmonary vein ostia in a left atrium 110, in order to electrically isolate pulmonary veins 80 from the rest of the heart. Enhanced ablation and scarring is achieved by creating a reflective region in the vicinity of the tissue designated for ablation, such that ablating ultrasound waves are reflected back from the reflective region and pass again through the ablation site.

As shown in FIG. 3A, reflection-facilitation element 12 is used to provide an extramyocardial reflective region 112, typically within pericardium 70 or between the pericardium and the myocardium. Typically, reflection-facilitation element 12 is transthoracically delivered using percutaneous subxiphoid access to the epicardium. For some applications, reflection-facilitation element 12 may comprise gas-delivery element 90, as described hereinabove with reference to FIGS. 2C-F, which is used to inflate pericardium 70 with gas to create reflective region 112 which reflects the applied ultrasound waves. Alternatively, the reflection-facilitation element may use other techniques for providing reflective region 112, such as those described herein, e.g., with reference to FIGS. 2G or 2H.

FIG. 3A additionally shows transcatheter advancement of tool 20 into left atrium 110, and placement of tool 20 in a location adjacent to pulmonary vein ostia in accordance with some applications of the present invention. Tool 20 is shown in a collapsed state prior to application of energy by transducer 40. For some applications, a transseptal approach is used to advance tool 20 to left atrium 110, using catheter 22, as shown in FIGS. 3A-C. Alternatively, tool 20 may be advanced to left atrium 110 using a transapical approach, via the apex of the left ventricle and the mitral valve (approach not shown). Further alternatively, tool 20 may be advanced to left atrium 110 via the aorta, the left ventricle, and the mitral valve (approach not shown). For some applications, tool 20 is first advanced into the left atrium, and extramyocardial reflective region 112 is subsequently provided, while for other applications, region 112 is first provided.

FIG. 3B shows the opening of tool 20 into an operative state within a left atrium of the heart. Tool 20 is located adjacent to a pulmonary vein ostium, and to tissue of atrial wall 100. Hinge 44 typically facilitates deflection of arm 30, such that arm 30 is deflected laterally from a position that is aligned with a longitudinal axis of tool 20. Deflection of arm 30 brings ultrasound transducer 40 into the proximity of cardiac tissue designated for ablation treatment, such that ultrasound transducer 40 is aimed at the designated site.

For some applications, as mentioned above, distal portion of tool 20 is telescopically extended into the pulmonary vein, such that anchoring element 48 (e.g., inflatable element 50) is disposed within a lumen of pulmonary vein 50. Anchoring element 48 is shown comprising inflatable element 50, which is shown inflated, applying pressure to a wall of the pulmonary vein, in order to stabilize and maintain tool 20 in place during application of treatment energy. Alternatively, anchoring is not provided, or other anchoring techniques are used, such as described herein. An exploded view of ultrasound transducer 40 shows the initiation of treatment by applying ablating ultrasound waves to the tissue of atrial wall 100.

FIG. 3C shows the rotation of arm 30 to successively aim ultrasound transducer 40 at a plurality of sites on atrial wall 100, typically to form a complete circular lesion 114, thereby electrically isolating pulmonary vein 80 from left atrium 110.

It is to be noted that system 10 can be used to treat other types of cardiac arrhythmia such as ventricular tachycardia. For such applications, tool 20 is advanced into a ventricle of a subject and lesions are created by ablation of tissue in the ventricle by application of ultrasound energy in accordance with applications of the present invention.

Reference is again made to FIGS. 1A-3C. For some applications ultrasound transducer 40 is configured to transmit ultrasound energy that is capable of damaging tissue by a variety of mechanisms, e.g., ablation and/or cavitation and/or standing waves or a combination thereof.

For some applications, the ultrasound HIFU energy application techniques described herein are practiced in combination with other types of ablation, such as cryoablation and/or radiofrequency (RF) ablation.

It is also to be noted that application of treatment energy to sites within a chamber of the heart is not limited to blood vessel orifices but may be applied to any region in the heart which is involved in triggering or maintaining cardiac arrhythmias.

Reference is again made to FIGS. 1A-3C. Phrenic nerve damage is an undesired yet potential complication of catheter-based ablation procedures including ablation by ultrasound energy, as described in Sacher et al. (2007) (referenced above). Some applications of the present invention reduce the potential of damage to the phrenic nerve, e.g., to the left phrenic nerve, which is located in proximity to the left atrial appendage. Typically, for applications in which reflection-facilitation element 12 delivers gas to inflate the pericardium, the gas typically distances the phrenic nerve from the site of ablation and creates a gas-filled barrier between the phrenic nerve and the ablation site, thereby protecting the phrenic nerve from potential damage by the applied ultrasound energy.

Additionally or alternatively, some applications of the present invention reduce potential damage to the esophagus that may be caused by ablation procedures performed on the heart. Typically, for applications in which reflection-facilitation element 12 delivers gas to inflate the pericardium, the gas creates a gas-filled barrier between the esophagus and the ablation site, thereby protecting the esophagus from potential damage by the applied ultrasound energy.

For some applications, system 10 is configured to continuously or periodically monitor the treated tissue during treatment, in order to assess whether the ablation is sufficient. For some applications, the system performs the monitoring by electrical mapping of the tissue, such that conductance of electrical signals is mapped and the need for further treatment is assessed. For some applications, a multi-electrode catheter for mapping of conductance following application of treatment is used.

For some applications, system 10 monitors the treated tissue using ultrasound, typically to detect the temperature of the treated tissue. Various ultrasonic parameters are dependent on the temperature of the tissue. For example, the speed of sound is dependent on the temperature of the tissue. In the case of a muscle (or atrial wall), the speed of sound increases as the temperature is elevated. Thus the time of flight (TOF) decreases as the temperature is elevated, assuming that the distance that the sound waves travel is fixed. The beating heart is more complicated, since due to atrial contraction the distance changes (even if the transducer is fixed in the same position or distance from the atrial wall). However, the distance change is predictable, and thus, for some applications, is used to extract the temperature change, as described below. For some applications, the ultrasonic parameter is selected from the group consisting of: an amplitude of the ultrasound energy applied by the ultrasound transducer and reflected by the reflective region, a scatter intensity of the reflected ultrasound energy, sub-harmonics of the reflected ultrasound energy, second and higher harmonic reflections of the reflected ultrasound energy, an attenuation of the reflected ultrasound energy, and a non-linear parameter of the reflected ultrasound energy.

Figure 4A:
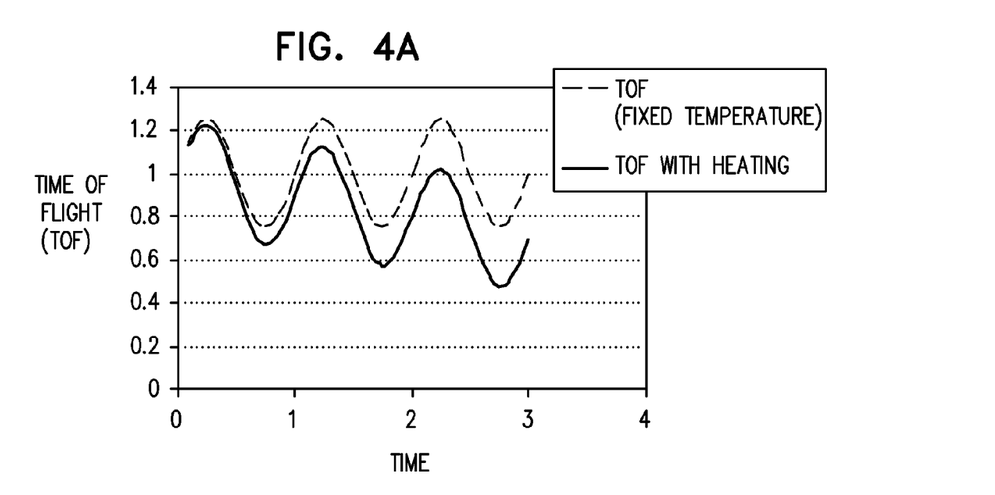
FIGS. 4A-B are graphs showing changing parameters in cardiac tissue resulting from heating of the tissue, as determined by simulated ultrasound monitoring, in accordance with some applications of the present invention.
Figure 4B:
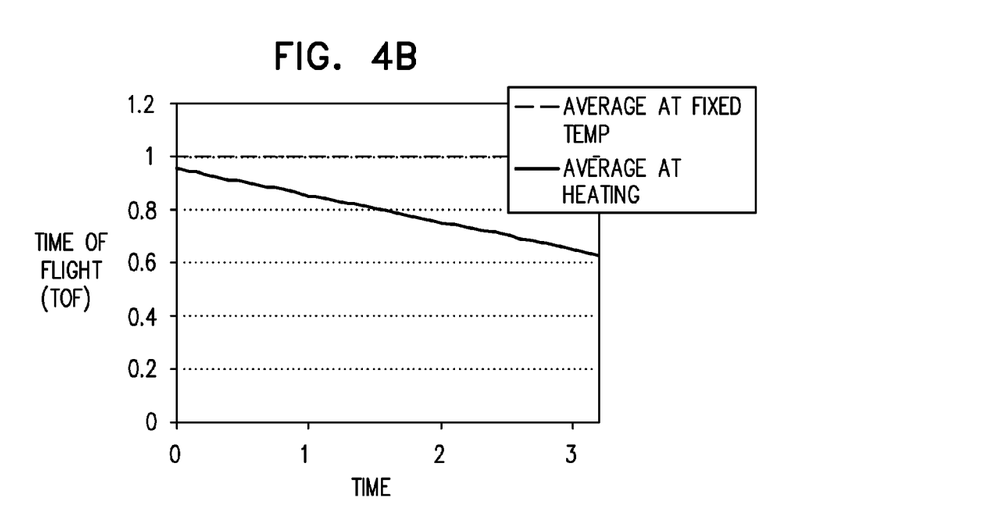

FIGS. 4A-B are graphs showing changing parameters in cardiac tissue resulting from heating of the tissue as determined by simulated ultrasound monitoring, in accordance with an application of the present invention (all units are arbitrary units (AU)). For some applications, ultrasound is used to monitor the treatment. For these applications, waves reflected by a reflective region in the tissue, e.g., a gas between the pericardium and atrial wall, are detected by ultrasound transducer 40, and the time of flight (TOF) is then measured. Changes in the time of flight (TOF) can be used as an indicator for proper heating of the tissue, in accordance with some applications of the present invention.

The graph in FIG. 4A shows a dashed line representing time of flight (TOF) in cardiac tissue under normal, untreated conditions. The TOF exhibits generally sinusoidal behavior due to contractions of the atrium. As described above, as a result of heating of a muscle, e.g., cardiac muscle, the speed of sound in the muscle typically increases. The continuous line in FIG. 4A represents (simulated) TOF in muscle tissue that has been heated by ultrasound energy applied thereto. The changes in TOF enable ultrasound monitoring of the treatment applied, in accordance with applications of the present invention.

The graph in FIG. 4B shows the result of signal processing of the TOF parameter, in accordance with an application of the present invention. The processing includes generating an average moving window having a width equal to a period of the beating heart (i.e., the heart rate). The dashed line shows a case with no heating, and the solid line shows a case that includes heating. Using an average moving window, the sinusoidal behavior is eliminated and the inclination of the TOF is obtained, thus monitoring the temperature of the ablation.

When the monitored temperature shows that the target temperature has been obtained, the ultrasonic transmission is ceased, and the transducer is rotated to a different radial location, either manually by the physician, or by a motor, e.g., driven by a control unit of system 10.

For some applications, system 10 alternatively or additionally measures other ultrasonic parameters, such as the amplitude of reflected ultrasonic waves, scatter intensity, sub-harmonics, second and higher harmonic reflections, attenuation and/or non-linear parameters. The system uses these measured parameters as indicative of change in the treated tissue. When sufficient change is obtained, the ultrasonic transmission is ceased and the transducer rotated, either manually by the physician, or by a motor, e.g., driven by a control unit of system 10.

It is noted that inflatable element 50, the telescopic expansion of distal portion 32 of tool 20, arm 30, and the 360 rotation of tool 20 are described hereinabove by way of illustration and not limitation, and the scope of the present invention includes a system that includes only some, or none, of these elements.

Figure 5:
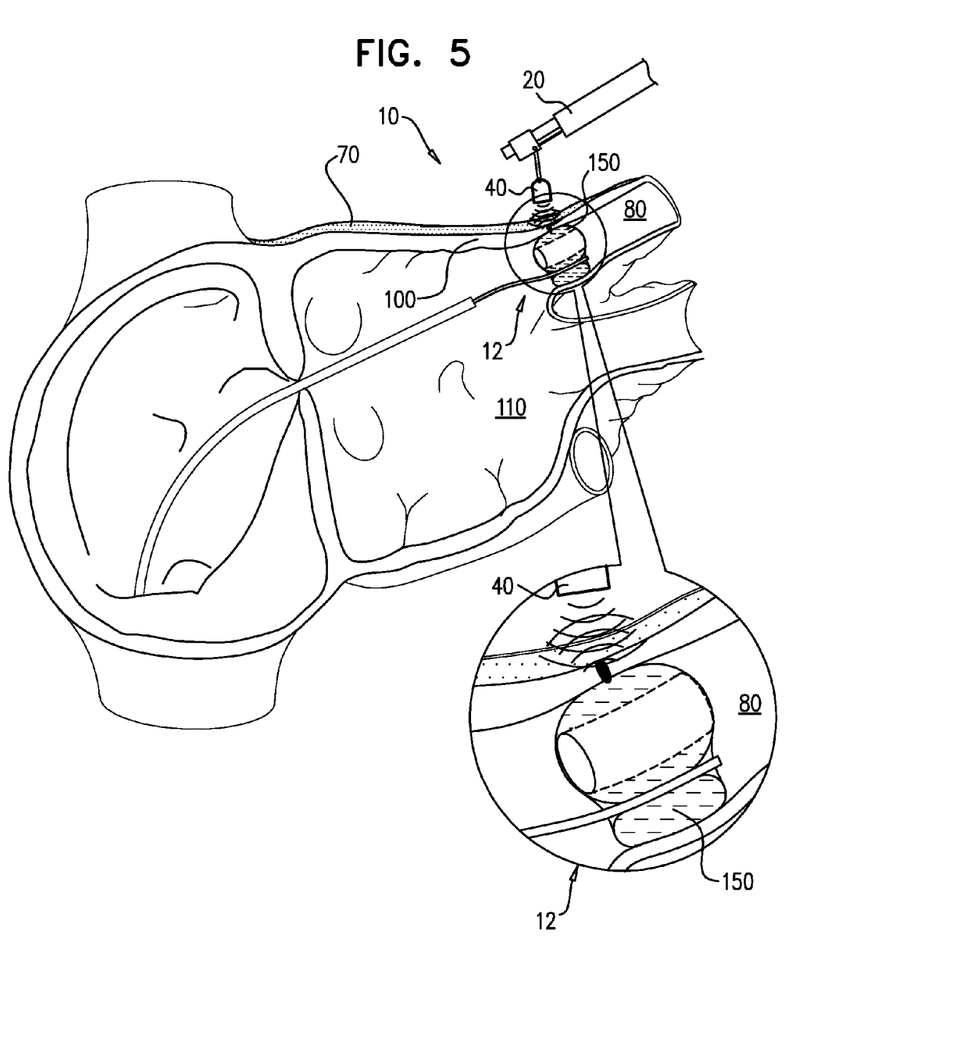
FIG. 5 is a schematic illustration of an alternative configuration of the system of FIGS. 1A-B, in accordance with an application of the present invention.

Reference is now made to FIG. 5, which is a schematic illustration of an alternative configuration of system 10, in accordance with an application of the present invention. In this configuration, ablation tool 20 is configured to apply ultrasound energy to a series of areas on the heart wall from a location outside of the heart, such as against or near an outer surface of the pericardium. Reflection-facilitation element 12 is configured to be placed inside the left atrium, to provide the reflective region within the atrium. For example, the reflection-facilitation element may comprise an inflatable element 150, such as described hereinabove with reference to 2H, mutatis mutandis, or a shaped acoustic reflector, such as described hereinabove with reference to 2G, mutatis mutandis. Optionally, the inflatable element is shaped so as to define a passage therethrough to allow the flow of blood.

Although techniques of the present invention have generally been described herein as being applied to cardiac tissue, these techniques may additionally be used, mutatis mutandis, to treat other tissue of a subject, such as liver tumors or varicose veins. The techniques are used to provide a reflective region at a far side of the tissue, by placing a reflective-facilitation element at the far side, and to ablate the tissue by applying ultrasound energy to a near side of the tissue such that at least a portion of the applied energy is reflected onto the tissue by the reflective region.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method comprising:
advancing, into a heart chamber of a subject, an ultrasound tool that includes at least one ultrasound transducer;
providing a reflective region at an extramyocardial site of the subject; and
activating the ultrasound transducer to ablate myocardial tissue by applying ultrasound energy to the myocardial tissue such that at least a portion of the transmitted energy is reflected by the reflective region onto the myocardial tissue of the subject,
wherein the extramyocardial site is within a pericardial region of the subject that consists of one or more regions selected from the group consisting of: a region between a pericardium of a heart of the subject and a myocardium of the heart, a region between a visceral pericardium of the heart and a parietal pericardium of the heart, and a region outside the pericardium and in contact therewith, and wherein providing the reflective region comprises providing the reflective region within the pericardial region.

2. The method according to claim 1, wherein advancing the ultrasound tool comprises temporarily stabilizing the ultrasound tool in the chamber using an anchoring element.

3. The method according to claim 1, wherein providing the reflective region comprises delivering a gas to the extramyocardial site.

4. The method according to claim 1, wherein providing the reflective region comprises inflating an inflatable element at the extramyocardial site with a fluid selected from the group consisting of: a gas, and a mixture of a liquid and a gas.

5. The method according to claim 4, wherein the selected fluid is a gas, and wherein providing the reflective region comprises inflating the inflatable element at the extramyocardial site with the gas.

6. The method according to claim 1, wherein providing the reflective region comprises delivering an acoustic reflector to the extramyocardial site.

7. The method according to claim 1, wherein providing the reflective region comprises inserting a mechanical surgical retractor into the extramyocardial site.

8. The method according to claim 1, wherein activating further comprises monitoring an ultrasonic parameter of the myocardial tissue.

9. The method according to claim 8, wherein activating further comprises performing an analysis of the parameter, and, responsively to the analysis, ceasing ablating the myocardial tissue.

10. The method according to claim 8, wherein the parameter is a time of flight of the ultrasound energy applied by the ultrasound transducer and reflected by the reflective region.

11. The method according to claim 10, wherein monitoring comprises using signal processing to eliminate sinusoidal behavior exhibited by the time of flight due to atrial contractions.

* * * * *